United States Patent
Fang et al.

(10) Patent No.: US 7,218,770 B2
(45) Date of Patent: May 15, 2007

(54) BALL GRID ARRAY MODELING FOR INSPECTING SURFACE MOUNTED DEVICES

(75) Inventors: Tong Fang, Old Bridge, NJ (US); Ming Fang, Princeton Jct., NJ (US)

(73) Assignee: Siemens Corporate Research, Inc., Princeton, NJ (US)

( * ) Notice: Subject to any disclaimer, the term of this patent is extended or adjusted under 35 U.S.C. 154(b) by 836 days.

(21) Appl. No.: 10/379,308

(22) Filed: Mar. 4, 2003

(65) Prior Publication Data

US 2004/0175029 A1 Sep. 9, 2004

(51) Int. Cl.
*G06K 9/00* (2006.01)
(52) U.S. Cl. .................................................. 382/145
(58) Field of Classification Search ................ 382/103, 382/141, 145, 147, 151, 152, 209, 218; 348/86, 348/92, 95
See application file for complete search history.

(56) References Cited

U.S. PATENT DOCUMENTS 6,151,406 A * 11/2000 Chang et al. ............... 382/147
6,396,942 B1 * 5/2002 Chang et al. ............... 382/141
6,614,926 B1 * 9/2003 Fix et al. .................... 382/150
7,013,038 B1 * 3/2006 Patnaik ....................... 382/145

OTHER PUBLICATIONS

Cognex Corp. "BGA II Inspection Package", pp. 1-4, 2001.*
Yu, et al. "New Approach To Vision-Based BGA Package Inspection", IEEE, pp. 107-1110, Nov. 2002.*

* cited by examiner

*Primary Examiner*—Daniel Mariam
(74) *Attorney, Agent, or Firm*—Donald B. Paschburg; F. Chau & Associates, LLC (57) ABSTRACT

A computer-implemented method for inspecting BGA components using a ball grid array model thereof in semiconductor surface mounted devices. The method comprises setting a plurality of regions of interest (ROIs) for all BGA balls to be modeled, building a first grid model that includes coordinates and a diameter of the BGA balls in the plurality of ROIs, setting a plurality of regions of interest (ROIs) containing a BGA body to be modeled, detecting four body boundaries to localize four corner coordinates, determining a body orientation from orientations of four boundaries, calculating an orientation of each boundary by the projection of the edge of boundary, and comparing the BGA components with an obtained BGA model to inspect the BGA components based on ball sizes and ball distributions.

26 Claims, 8 Drawing Sheets

BALL GRID ARRAY MODELING FOR INSPECTING SURFACE MOUNTED DEVICES

BACKGROUND

1. Field of the Invention

The present invention relates to a method for packaging surface mounted devices, and more particularly to modeling a ball grid array (BGA) for inspecting BGA applied electronic devices.

2. Discussion of Related Art

The on-chip delay of signals communicating among components within IC semiconductor devices has been reduced rapidly in the past few years. However, the signal delay in packaged ICs has not been reduced as much as that of the on-chip ICs. This is partly due to the focus of semiconductor industry on fabrication process rather than packaging. Packaging signal loss can be reduced by increasing the packaging density. To this end, a new chip packaging technology called 'Ball Grid Array' (BGA) was developed. With BGA chips, more electrical connections between chips and printed boards can be made because the electrical connections are on the under-side of the chip, freeing up more space than the conventional chips having surround edge connections.

There are many ways to inspect BGA chips. Inspection by illumination inspection, a low-power lens or stereo microscope is the most common. Two dimensional (2-D) systems using a camera to capture and digitize the optical image into a gray scale image represent an improvement over aided human vision. Three dimensional surface illumination systems generally use either structured light or laser scanning to generate height information along with a gray-scale image. While these systems tend to provide more surface data for analysis, they tend to be less sensitive to lighting conditions. The disadvantage of BGA packaging is that visual inspection is no longer available because, once the chip is attached to the circuit board, the electrical connections are hidden under the package. An automated x-ray inspection system that uses cross-sectional images to analyze both single-sided and double-sided surface mount assembly circuit cards has been developed for inspecting hidden parts of the package. However, the automated x-ray inspection system is elaborate and complicated. Further, a common problem of the inspection methods and systems described above is that a comparatively large amount of time is needed to inspect all BGA components.

Instead of an X-ray inspection system, an accurate model of the BGA package can be used to facilitate inspection of the BGA package. A need, therefore, exists for an accurate model of the BGA, having information about the geometric structures and properties of the SMD component.

SUMMARY OF THE INVENTION

The present invention is directed to a computer-implemented method for inspecting BGA components using a model thereof in semiconductor surface mounted devices. According to an embodiment of the present invention, the method comprises building a ball grid array (BGA) balls model to obtain geographic information of the BGA balls based on a gray scale image for a common BGA component; generating a ball gird array (BGA) body model from images obtained through image processing and extraction process; and comparing the BGA components with a BGA model to inspect the BGA components based on ball positions, diameter, inter-ball distance, a total number of the BGA balls, body size, or body orientation, wherein the BGA model includes the BGA balls model obtained by the step of building and the BGA body model obtained by the step of generating.

The ball grid array (BGA) balls model is achieved by setting a plurality of regions of interest (ROIs) for all BGA balls to be modeled through a BGA ball detection process, and building a grid model that includes a grid orientation, a grid horizontal displacement, a grid vertical displacement, the maximum number of balls in a row/column, and a coordinate of a top-left corner ball center. If at least one ball is detected inside of ROIs, a BGA ball information is extracted by calculating a ball center coordinate and a diameter of each detected ball.

Building a BGA balls model further comprises determining a grid horizontal displacement and a grid vertical displacement. The grid horizontal displacement is determined based on the maximum frequency of the minimum horizontal distance histogram by using the minimum horizontal distance of each ball located inside the maximum bin of the histogram and the total number of balls located in the maximum frequency bin of the histogram. Likewise, the grid vertical displacement is determined based on the maximum frequency of the minimum vertical distance histogram by using the minimum vertical distance of each ball located inside the maximum bin of the histogram and the total number of balls located in the maximum frequency bin of the histogram. Preferably, the BGA ball orientation is obtained based on a ball horizontal angle and a ball vertical angle.

In this embodiment, a BGA top-left corner coordinate is determined which is defined as the intersection of a first row gird line and a first column grid line, wherein the first row grid line is generated by connecting the centers of the first ball and the last ball in the first row, the first column grid line being generated by connecting the centers of the first ball and the last ball in the first column.

Preferably, the modeling of the ball grid array further comprises: fine-tuning a horizontal inter-ball distance and a vertical inter-ball distance by averaging inter-ball distances of all rows/columns to further tune BGA model parameters; fine-tuning a BGA ball orientation by averaging each horizontal angle and each vertical angle, wherein the first and last balls in each row/column are used to have the longest distance; and fine-tuning the BGA top-left corner coordinate by using local and global BGA ball contrast calculation. All BGA balls are localized by verifying whether there is a ball on the grid intersection and the modeling of the grid array is completed by combining the information of the grid model and the information of BGA ball positions and diameters. Preferably, verifying is performed using dominant circle detection process.

Then, generating a ball gird array (BGA) body model is provided which comprises the steps of setting regions of interest (ROIs) containing a BGA body to be modeled and detecting four body boundaries to localize four corner coordinates. A body orientation is determined based on orientations of four boundaries after an orientation of each boundary is calculated by the projection of the edge of boundary. Then, four boundaries of the body are localized to obtain four corner coordinates for modeling the GBA body by calculating intersection positions of two adjacent boundary lines.

According to another embodiment of the present invention, a computer-implemented method is provided for modeling ball grid array (BGA) balls in semiconductor surface mounted devices, comprising: setting a plurality of regions of interest (ROIs) for all BGA balls to be modeled through a BGA ball detection process; building a grid model that includes a grid orientation, a grid horizontal displacement, a grid vertical displacement, the maximum number of balls in a row/column, a coordinate of the top-left corner ball center; localizing all BGA balls and determining their diameters; and combining the grid model with locations and diameters of all the balls to create a BGA ball model.

According to another embodiment of the present invention, a computer-implemented method is provided for modeling a ball grid array (BGA) body in semiconductor surface mounted devices, comprising the steps of: setting a plurality of regions of interest (ROIs) containing a BGA body to be modeled; performing orientation determination for left, top, right and bottom edges to obtain corresponding edge orientation; and localizing four corner coordinates to detect four body boundaries by calculating intersection positions of two adjacent boundary lines.

BRIEF DESCRIPTION OF THE DRAWINGS

A more complete appreciation of the invention, and many of the attendant advantages thereof, will be readily apparent with reference to the following detailed description when considered in conjunction with the accompanying drawings in which like reference symbols indicate the same or the similar components, wherein.

DETAILED DESCRIPTION OF PREFERRED EMBODIMENTS

Preferred embodiments of the present invention will now be described hereinafter with reference to the accompanying drawings. The present invention may, however, be embodied in many different forms and should not be construed as limited to the embodiments set forth herein.

It is to be understood that the systems and methods described herein in accordance with the present invention may be implemented in various forms of hardware, software, firmware, special purpose processors, or a combination thereof. Preferably, the present invention is implemented in software as an application comprising program instructions that are tangibly embodied on one or more program storage devices (e.g., magnetic floppy disk, RAM, CD Rom, ROM and flash memory), and executable by any device or machine comprising suitable architecture.

It is to be further understood that since the constituent system modules and method steps depicted in the accompanying Figures are preferably implemented in software, the actual connection between the system components (or the flow of the process steps) may differ depending upon the manner in which the present invention is programmed. Given the teachings herein, one of ordinary skill in the related art will be able to contemplate these and similar implementations or configurations of the present invention.

Figure 1:
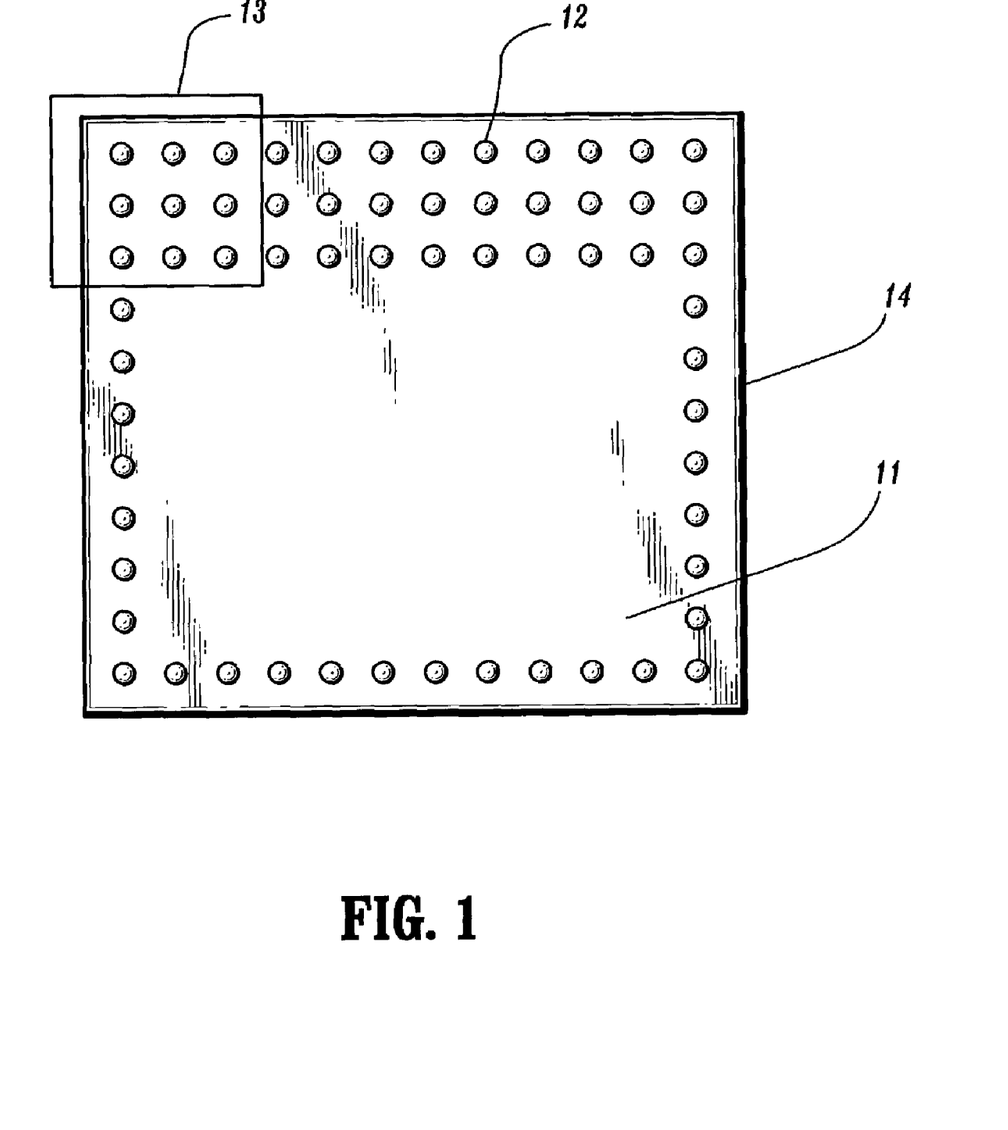
FIG. 1 illustrates a set of regions of interest (ROIs) in a BGA component for modeling BGA balls.

FIG. 1 illustrates a set of regions of interest (ROIs) in a BGA component for modeling BGA balls. A ball grid array (BGA) chip 11 is one of the common surface mounted device (SMD) components containing balls 12 and a body 14. All BGA balls are in general located within the BGA body boundary on a regular grid. To describe a BGA component completely, the model should at least contain geometric information of all BGA balls and the BGA body, which includes the positions, diameter, and the inter-ball distance of all balls, as well as the total number of balls and body's size, orientation and location. Because of the distinct nature of BGA balls and body boundary, BGA modeling can be divided into the following two parts: the BGA ball modeling and BGA body modeling.

Figure 2:
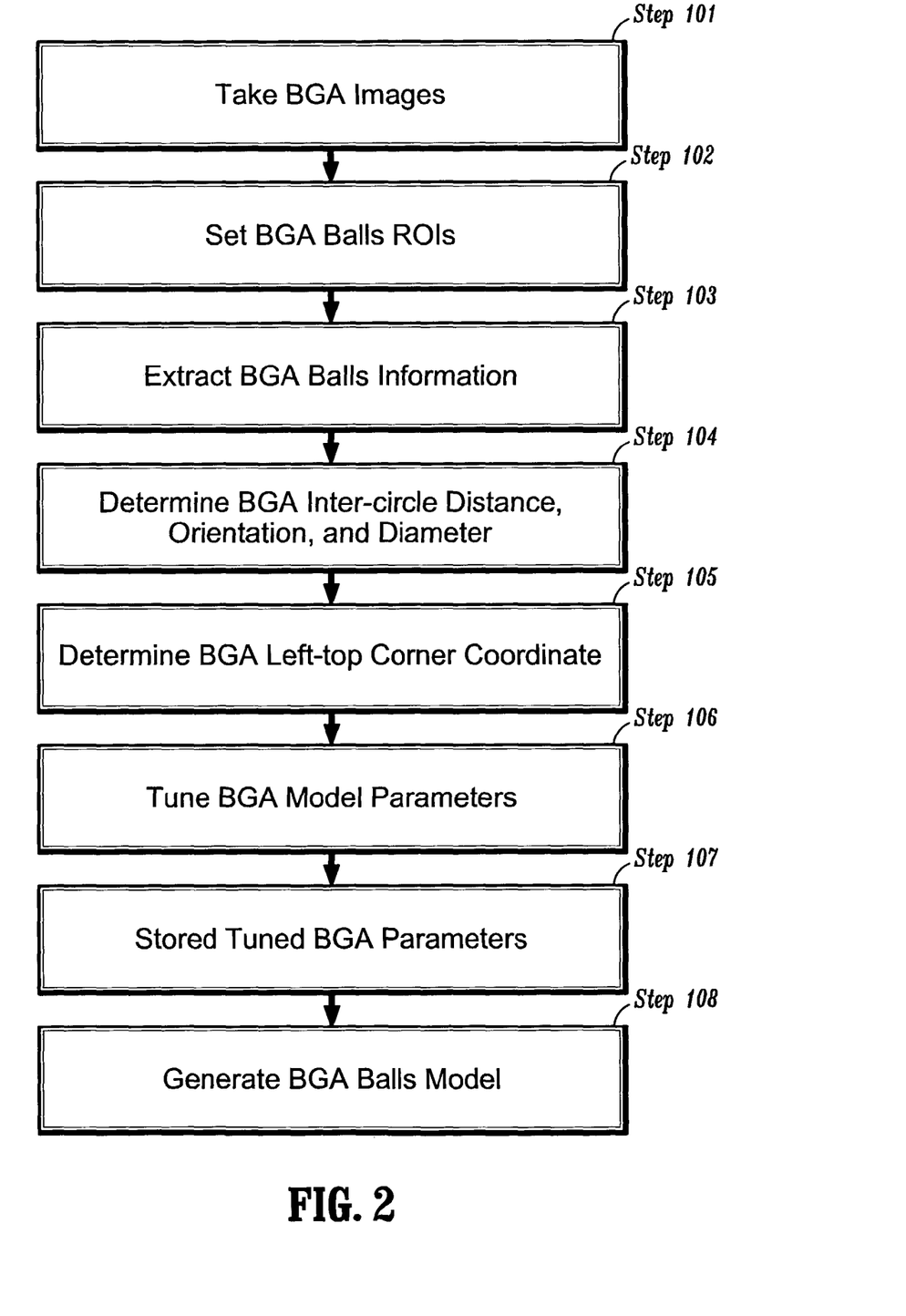
FIG. 2 is a flow chart illustrating an overall process of modeling a BGA ball according to an embodiment of the present invention.

FIG. 2 is a flow chart illustrating an overall process of modeling BGA balls according to an embodiment of the present invention. The SMD component model can be generated either from a CAD data file describing the SMD component or from one to two images of the SMD component. Here, a SMD component model is generated from images. Typically, a SMD model is directly extracted from 1 or 2 images of a SMD component through some image processing and extraction techniques (step 101).

To model BGA balls from a grayscale image for a common BGA component, a Region of Interest (ROI) 13 containing all BGA balls on the image must be set (step 102). In some cases, given ROIs may not actually include the BGA balls. However, each BGA ball to be modeled is assumed to be completely included in the ROIs, as seen in FIG. 1. In the beginning, it is also assumed that all BGA balls have the same diameter and an equal inter-ball distance at step 102. Preferably, a BGA component image contains only one BGA component, and the centers of all the BGA balls are located on a regular grid.

Figure 3:
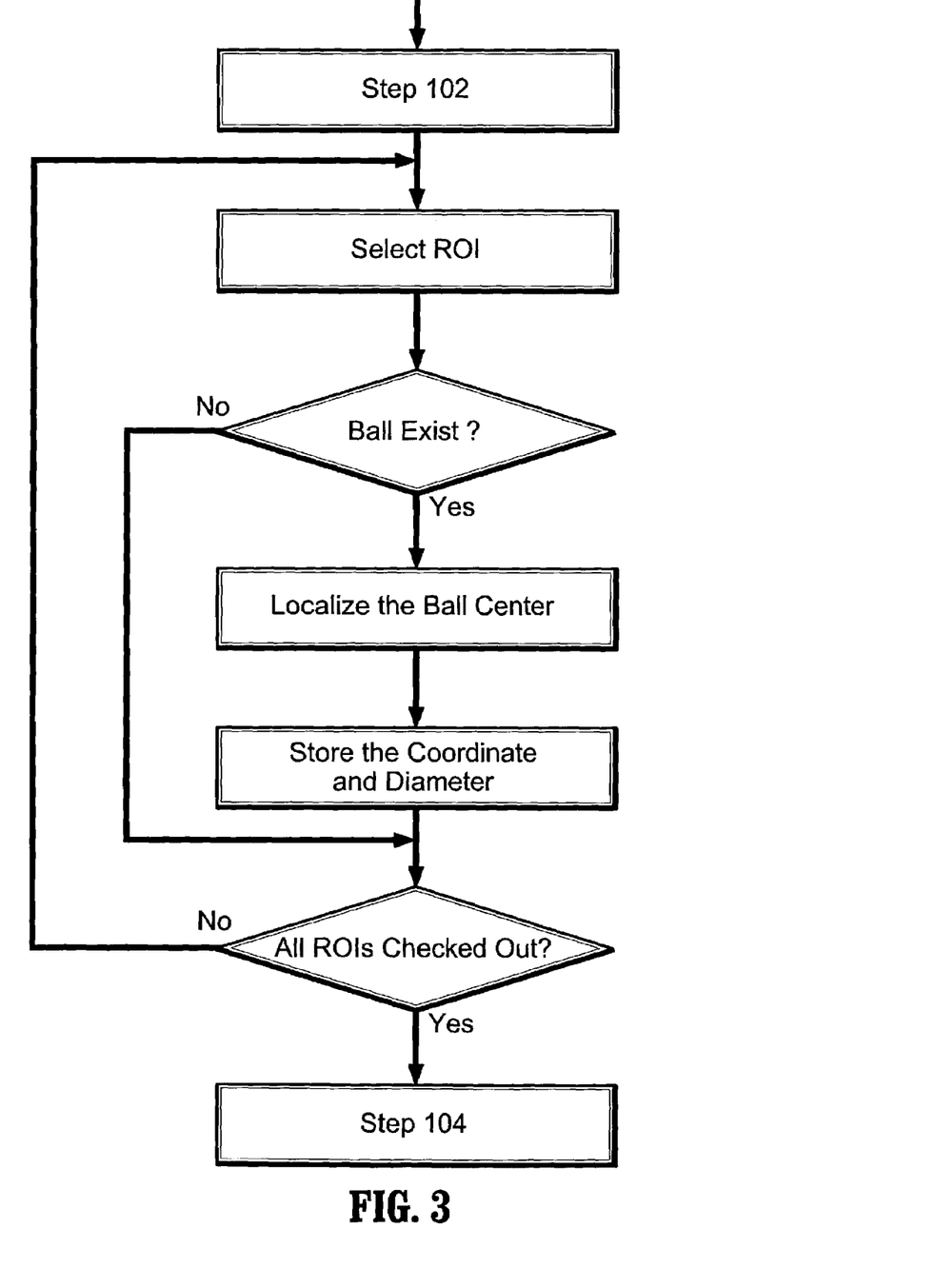
FIG. 3 is a flow chart for more detailed explanation of a BGA ball information extraction process shown at step 103 of FIG. 2.

FIG. 3 shows a more detailed explanation of BGA ball information extraction process of step 103 (FIG. 2). It is determined according to a dominant circle detection process whether there is a ball in a given ROI. Since the dominant circle detection process is well known to ordinary persons of skill in this art, detailed explanation of the dominant circle detection process will be omitted. If a ball exists in the given ROI, a ball center is localized to get a coordinate of the ball, and a ball diameter is calculated to build a preliminary grid model. Such information on the ball center (a coordinate of the ball) and the diameter of the ball is stored in a device independent packet format (DIPF) based on the industry standard extensible markup language (XML) in an internal memory. This ball information extraction operation is repeated until ROIs are all checked out.

Figure 4:
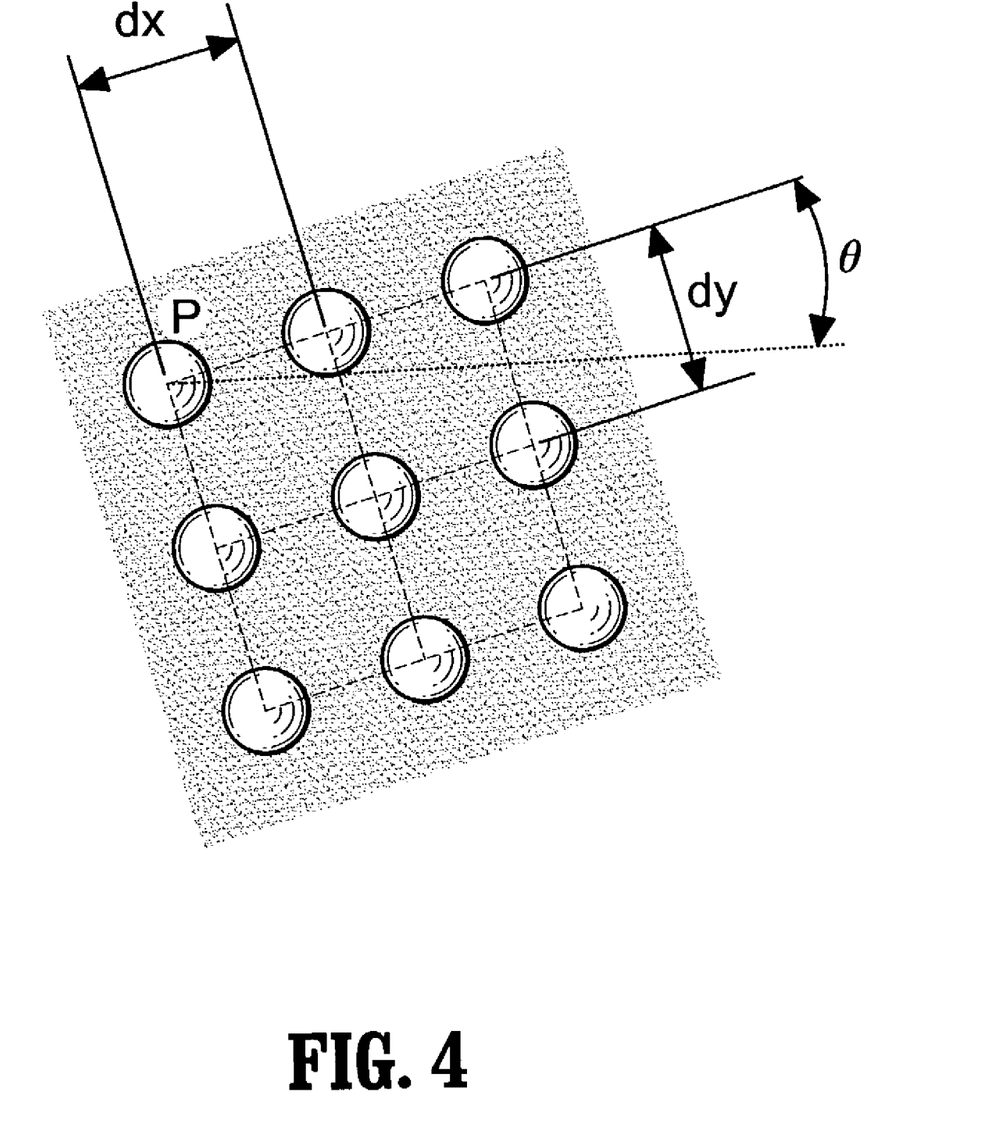
FIG. 4 is a portion of ROIs for building a grid model that includes a grid orientation, a grid horizontal displacement, a grid vertical displacement, and a grid top-left corner.

Referring to FIG. 2 and FIG. 4, obtaining a refined grid model (steps 104 and 105 of FIG. 2) will now be described. Based on center coordinates of all detected BGA balls obtained through step 103, the preliminary grid model can be refined. A refined grid model is defined to have a horizontal and vertical ball distance (grid displacement), a ball orientation, and a top-left corner coordinate. It is assumed that most BGA balls on a grid intersection have at least one horizontal adjacent ball and one vertical adjacent ball.

The distance between a ball and its horizontal adjacent ball is the horizontal grid displacement (dx). The vertical grid displacement (dy) equals to the distance between a ball and its vertical adjacent ball. For each ball, its minimum horizontal and vertical distances with other balls are calculated, as well as its corresponding horizontal angle ($\theta_h$) and vertical angle ($\theta_v$) with its adjacent balls in horizontal and vertical directions. The horizontal distance of a ball is defined as the distance between the ball and another ball if the angle between the line connecting two ball centers and x-axis is in the range of [−45°, 45°]. Similarly, the vertical distance of a ball is defined as the distance between the ball and another ball if the angle between the line connecting two ball centers and x-axis is the range of [45°, 135°].

To calculate the horizontal inter-ball distance, the minimum horizontal distance histogram is generated. The x-axis of the histogram plot is the minimum horizontal distance, and the y-axis is the frequency (the number of balls which are inside a corresponding horizontal distance bin). Therefore, the horizontal inter-ball distance dx can be determined from the maximum frequency of the minimum horizontal distance histogram. That is, $$dx = \frac{\sum_{i=1}^{M} dmx_i}{M},$$

where $dmx_i$ is the minimum horizontal distance of the ith ball located inside the maximum bin of the histogram. M is the total number of balls located in the maximum frequency bin of the histogram. Similarly, the above method can also be used to calculate a vertical inter-ball distance dy, a ball horizontal angle $\theta_h$, a ball vertical angle $\theta_v$ and a ball diameter.

Based on the assumption that the sum of the horizontal angle $\theta_h$ and vertical angle $\theta_v$, is 90°, the average BGA ball orientation $\theta$ can be obtained as follows:

$$\theta = \frac{\theta_h + 90° - \theta_v}{2}.$$

From obtained horizontal/vertical inter-ball distances and a set of ball center information, the maximum number of balls in a row/column can also be determined.

A grid top-left corner is defined as the intersection of the first row grid line and the first column grid line, which is the top-left ball center if a ball exists. The first row grid line is generated by connecting the centers of the first ball and the last ball in the first row. Similarly, the first column grid line is generated by connecting the centers of the first ball and the last ball in the first column. Therefore, a top-left corner coordinate can be obtained and stored in a memory (step 105).

Parameters calculated through steps 104 and 105 are based on local inter-ball information. Therefore, the grid model parameters need to be fine-tuned to further improve the model accuracy by using as much ball information as possible. Using those parameters, a process for tuning a grid model will be described.

Fine-tuning inter-ball distance is performed to have a more accurate inter-ball distance based on the displacements obtained through step 104. Previously at step 104, the inter-ball distance was determined from the minimum distance of the centers of any two adjacent balls. From the refined grid model, the positions of the first ball and the last ball in a row/column and the number of balls in the row/column have been calculated. Therefore, a more accurate inter-ball distance $d_i$ of row/column i can be determined as follows:

$$d_i = \frac{\text{(distance between the centers of the first ball and the last ball)}_i}{\text{(maximum number of balls)}_i}.$$

By applying this formula, the horizontal/vertical inter-ball distance is calculated by averaging the inter-ball distances of all rows. That is:

$$dx = \frac{\sum_{i=1}^{N_{row}} dx_i}{N_{row}}, \text{ and } dy = \frac{\sum_{i=1}^{N_{col}} dy_i}{N_{col}},$$

where $N_{row}$ and $N_{col}$ are the total number rows and columns, respectively.

Fine-tuning BGA ball orientation is also performed to have a more accurate BGA ball orientation. Previously, the BGA ball orientation was calculated from centers of two adjacent balls in the same row/column. Because the distance of these two adjacent balls is short, a small error in the obtained ball center positions may lead to larger error in the calculation of ball orientation. In the fine-turning of BGA ball orientation, the first and last balls in a row/column are used because they have longest distance. If the $\theta_{hi}$, $\theta_{vj}$ are the ball orientation calculated from the row i and column j, separately, the horizontal angle $\theta_h$ and vertical angle $\theta_v$ can be determined as follows:

$$\theta_h = \frac{\sum_{i=1}^{N_{row}} \theta_{hi}}{N_{row}}, \text{ and } \theta_v = \frac{\sum_{j=1}^{N_{col}} \theta_{vj}}{N_{col}}.$$

Then, by applying $$\theta = \frac{\theta_h + 90° - \theta_v}{2}$$

again, the final ball orientation $\theta$ can be obtained.

For the same reason, Fine-tuning BGA top-left corner coordinate is performed. The top-left corner coordinate was preliminarily determined from the intersection of the first row grid line and the first column grid line. Actually, this coordinate is extracted by using only four ball centers. This parameter is refined by making full use of all the ball information.

As the grid model parameters are all fine-tuned except the top-left corner coordinate, exhaustive searching operation is performed to obtain the optimal top-left corner coordinates around the preliminarily determined corner coordinates so that the grid model can best fit the actual whole BGA ball pattern.

Measuring how well a grid model fits the BGA ball pattern is based on the local ball contrast calculation. The local image contrast of a BGA ball is obtained from the local image contrast around the circle edge area. If a ball position in the grid model is matched well with the actual ball position, the obtained contrast value of that ball will be the largest. Otherwise, due to the ball position shift in the grid model, the contrast value will be decreased. Therefore, by searching the maximum total contrast value for all balls, the best fit grid model and the optimal top-left corner coordinates can be determined.

Figure 5:
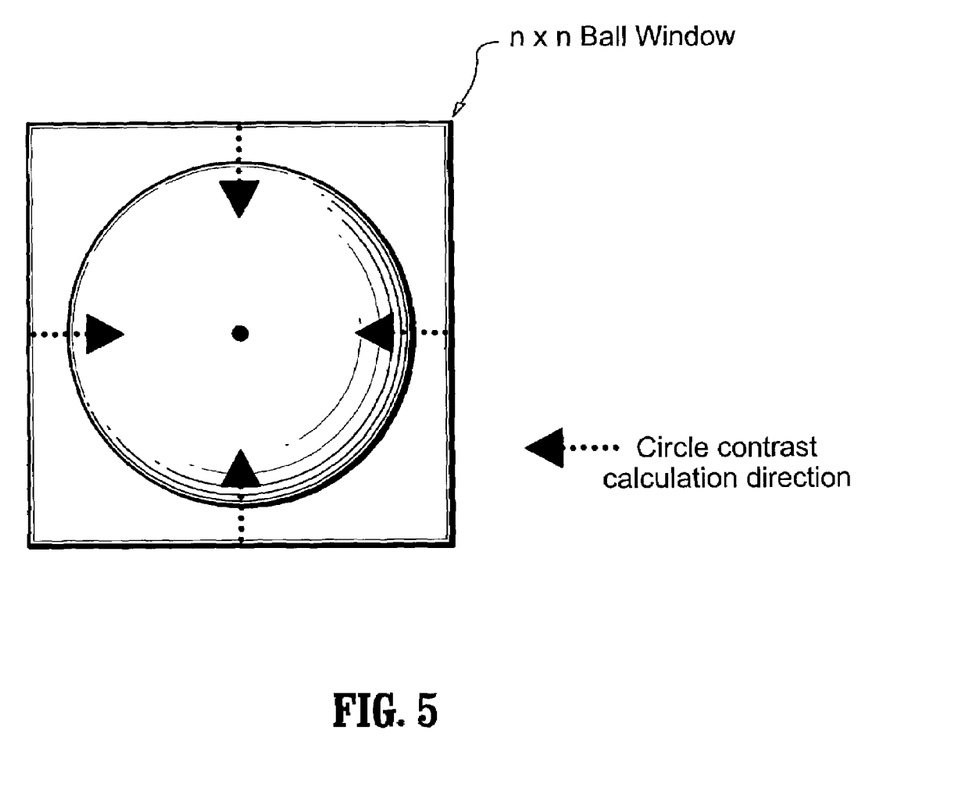
FIG. 5 is a n×n ball window in a ball grid array component for calculating local Image contrast of BGA balls.

Referring to FIG. 5, local Image contrast calculation of BGA balls will now be described. The local image contrast of a BGA ball is obtained from the local image contrast around the circle edge area. Since high local image contrast around the circle edge area in general means easier and more accurate circle edge localization, it leads to high confidence in the ball modeling process. The contrast of each ball is calculated by the gradient operation along the direction that is perpendicular to the circle tangent:

$$\Delta = \max |A(k) - A(k-1)|$$

For simplicity, only gradient operations along the horizontal and the vertical directions are considered, as shown by the four arrows in FIG. 5. In total, four local image contrast values of a circle, called left, right, top and bottom contrast, can be obtained. The final local image contrast value ($\delta_i$) of ith ball can be calculated as follows:

$$\delta_i = \frac{\Delta_{left} + \Delta_{right} + \Delta_{top} + \Delta_{bottom}}{4}.$$

Then, the local contrast value of all N BGA balls can be generated by $$\delta = \frac{\sum_{i=1}^{N} \delta_i}{N}$$

The constant k is determined from the BGA ball modeling experiments, which is set to 1.0 for the current BGA ball modeling application.

After the grid model is created, all BGA balls are localized by verifying whether there is a ball on the grid intersection. The ball verification is conducted by using the dominant circle detection algorithm. Positions and diameters of all balls existing in the BGA component are recorded. In addition, the ball diameter from the BGA model is calculated by averaging the diameters of all detected balls. Finally, a BGA model can be generated by combining the information of the grid model and the information of BGA ball positions and diameters (step 108).

Figure 6:
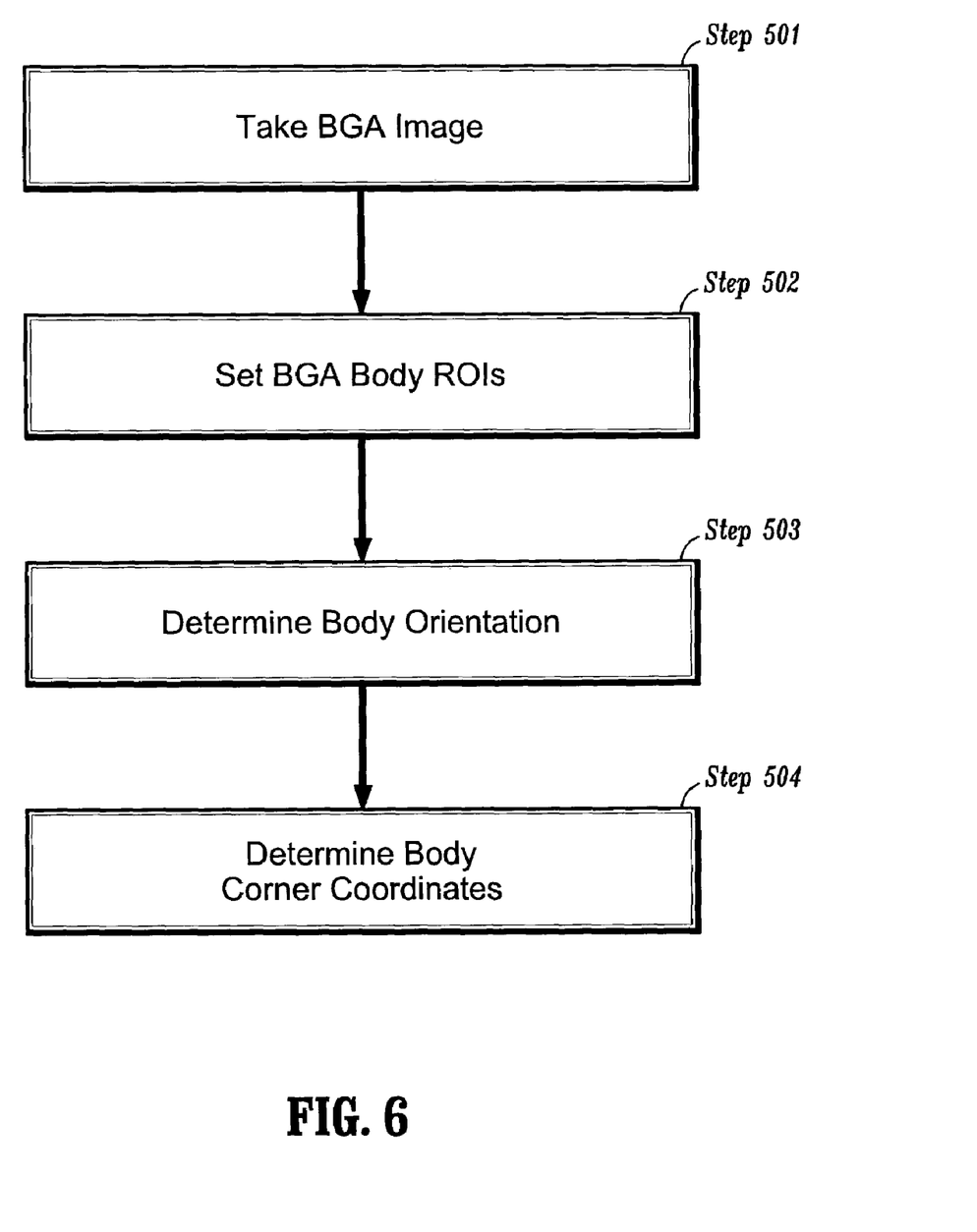
FIG. 6 is a flow chart illustrating an overall process of modeling a BGA body according to an embodiment of the present invention.

FIG. 6 is a flow chart illustrating an overall process of modeling a BGA body according to an embodiment of the present invention. Similar to modeling a BGA ball, a BGA body model is generated from images obtained through some image processing and extraction techniques (step 501). To model BGA body from a grayscale image for a common BGA component, a Region of Interest (ROI) containing all BGA body on the image has to be set (step 502). Typically, a shape of the BGA body to be modeled is a rectangle.

Figure 7:
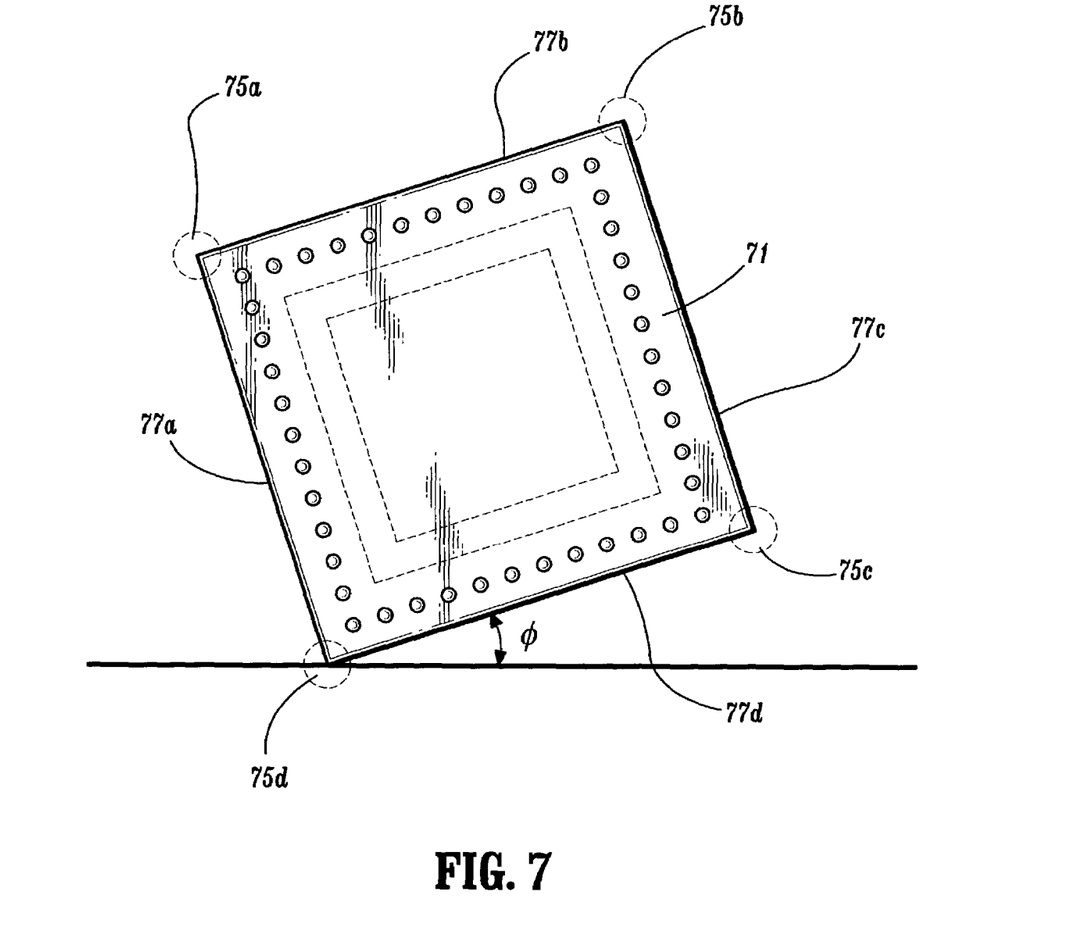
FIG. 7 is a schematic diagram for building a BGA body model that includes an orientation of the body and coordinates of four corners.

FIG. 7 is a schematic diagram for building a BGA body model that includes an orientation of a BGA body 71 and coordinates of four corners 75a, 75b, 75c, and 75d. Since the shape of the BGA body is a rectangle, positions of the four corner coordinates and a body orientation ($\phi$) are the elements of a BGA body model. To localize the four corner coordinates, four body boundary edge lines 77a, 77b, 77c, and 77d have to be detected first. The horizontal/vertical projection method is used as a basic technique for detecting the body boundaries and the body orientation.

The body orientation can be determined from the orientations of the four body boundary edge lines (step 504). The orientation of each boundary edge line can be calculated by the projection of each body boundary edge line as follows. Let $\phi$ is the orientation of a body boundary edge line. If an image is projected which only includes the edge along a radial line oriented at an angle of ($\phi+90°$), the maximum value $\Psi$ of the projection equals to the integral value of the body boundary edge line. However, $\Psi$ will be decreased when the edge is projected at ($\phi+90°\pm\Delta\phi$), where $\Delta\phi \neq 0$.

Assuming the orientation of a body boundary edge line is in the range of [$\phi_1$, $\phi_2$], the body boundary edge line can be projected from ($\phi_1+90°$) to ($\phi_2 90°$) and a profile of the maximum projection value at each angle can be obtained. Based on this, the body boundary edge line orientation $\phi$ can be determined by searching the peak value of the projection profile. That is:

$$\phi = \max(\Psi_{\phi i}), \text{ where } \phi_1 \leq \phi_i \leq \phi_2$$

To determine the body orientation, the four boundary edge lines of the BGA body 71 are identified by edge detection operation, and then orientation determination is performed for the left, top, right, and bottom body boundary edge lines, individually, and corresponding orientation of each body boundary edge line $\phi_{left}$, $\phi_{top}$, $\phi_{right}$, or $\phi_{bottom}$ can be obtained, separately. Finally, the body orientation can be calculated as follows:

$$\phi = \frac{(90 - \phi_{left}) + \phi_{top} + (90 - \phi_{right}) + \phi_{bottom}}{4}$$

With regard to obtaining body corner coordinates 75a, 75b, 75c, and 75d, the localization of four boundaries is a key to determine the coordinates of the four corners. Similar to the body orientation determination, the projection method is used to localize the boundaries.

After determining the body orientation ($\phi$), the image is projected which includes the top body boundary edge line, for example, along a radial line oriented at an angle of ($\phi+90$). From the projection profile, the maximum project value and its corresponding position on the projection line can be provided. Then, the top body boundary edge line position can be identified. Similarly, the left, right and bottom boundary line can be localized as well. Therefore, the body corner coordinates can be obtained by calculating the intersection position of two boundary lines. With the body orientation and four corner coordinates, the BGA body model can be generated.

Figure 8A:
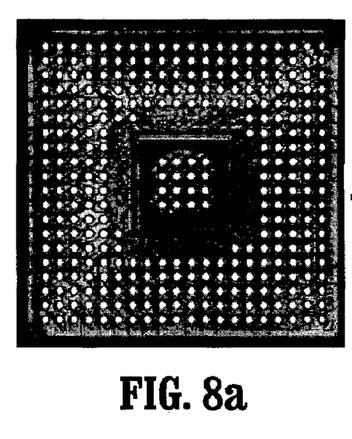
FIGS. 8, 9, and 10 show images containing components "BGA 2l1," "BGA Blau," and "BGA 3l1," respectively, before and after modeling a BGA ball component.
Figure 8B:
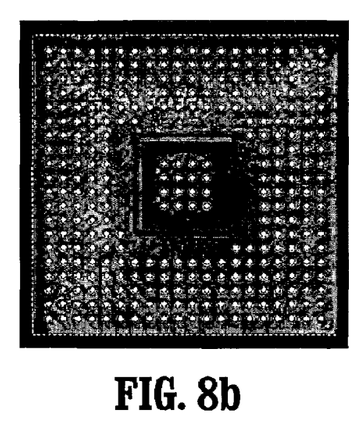
Figure 9A:
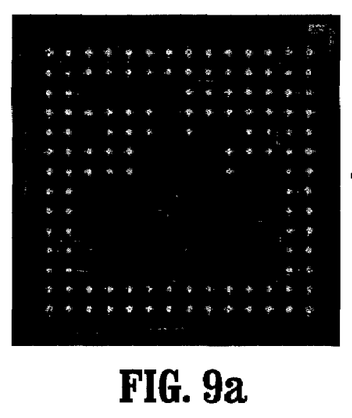
Figure 9B:
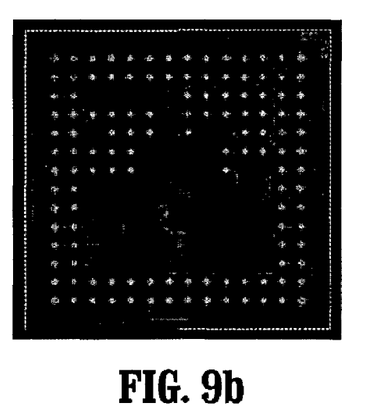
Figure 10A:
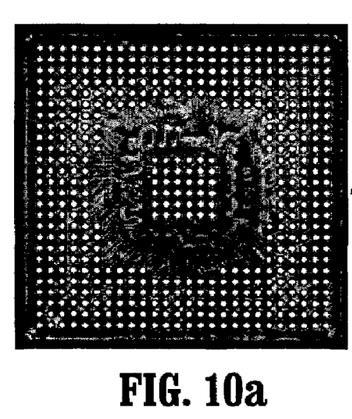
Figure 10B:
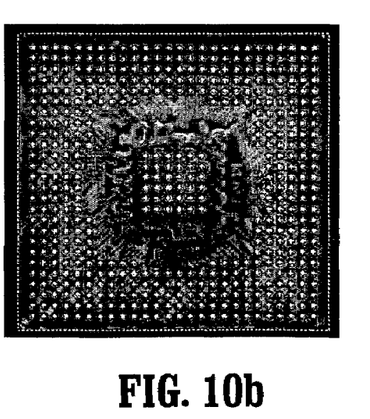

The methods for modeling the BGA body and ball modeling as discussed above have been successfully applied to BGA modeling applications. FIG. 8(a) shows an image containing component "BGA 211" before, and FIG. 8(b) after the modeling. FIG. 9 (a) displays an image of "BGA Blau" before, and FIG. 9(b) after the modeling. FIG. 10(a) displays an image of "BGA 311" before, and FIG. 10(b) after modeling.

As shown in FIGS. 8(a) and (b)–10(a) and (b), BGA modeling methods according to the present invention can be applied to a wide range of BGA components including different BGA component and ball sizes, different ball distributions, as well as different background conditions.

In BGA component modeling application, the BGA model is directly extracted from a BGA component image through image processing and extraction techniques. Where no geometric description about the BGA component is available before the model generation process, it is difficult to measure the correctness of the modeling results directly by comparing the extracted model to the real component. It is very helpful to give a confidence measure to indicate the confidence of the correctness of the extracted ball and body models. Therefore, to value the correctness of our modeling results, the confidences of BGA balls and body modeling are measured by using a BGA modeling confidence measurement method. The confidence measure values for the three examples are shown in Table 1.

TABLE 1

The confidence values of BGA ball and body modeling for three different BGA components

| | BGA type | | |
|---|---|---|---|
| Conf. Measures | BGA 2I1 | BGA Blau | BGA 3I1 |
| p of BGA ball | 0.9346 | 0.8486 | 0.9392 |
| p of BGA ball | 0.8996 | 0.7451 | 0.8678 |

From Table 1, it is noted that the both component BGA 2I1 and component BGA 3I1 have approximately the same confidence value (p). This is to be expected since the visual similarity of both BGA components is obvious, such as the illumination condition for the balls and bodies. In comparison, the confidence measure of BGA Blau is lower than that of BGA 2I1 or BGA 3I1. This is also easy to find that BGA Blau has a relatively poor illumination or difficult surface condition. Furthermore, the confidence measures of BGA body modeling are lower for all three testing components than those of BGA ball modeling. This indicates that the BGA body illumination and localization conditions are worse than those of BGA ball, which can easily be verified with the images shown in FIGS. 8–10. In addition, BGA Blau has the lowest confidence measure for body modeling, which indicates the most unfavorable illumination and localization condition for modeling the body of BGA Blau. That can again be seen very clearly from FIG. 9, where the very low image contrast in the body boundary regions makes the body localization and modeling less reliable.

While the present invention has been described in detail with reference to the preferred embodiments, those skilled in the art will appreciate that various modifications and substitutions can be made thereto without departing from the spirit and scope of the present invention as set forth in the appended claims.

What is claimed is:

1. A computer-implemented method for inspecting a ball grid array (BGA) of a semiconductor surface mounted device, the method comprising:
   providing an image of the BGA;
   generating a first geometric model of a plurality of balls of the BGA;
   generating a second geometric model of a body of the BGA, wherein the second model includes a body orientation of the BGA; and
   inspecting ball and body characteristics of the BGA on the basis of the first geometric model and the second geometric model.

2. The method of claim 1, wherein generating the first geometric model further comprises:
   setting a plurality of regions of interest (ROIs) for all BGA balls to be modeled; and
   building a first grid model that includes coordinates and a diameter of the BGA balls in the plurality of ROIs.

3. The method of claim 2, wherein the step of building the first grid model further comprises:
   detecting whether a ball exists in the inside of each ROI to extract ball information using dominant circle detection process;
   calculating a ball center coordinate and a diameter of each detected ball if a ball is detected; and
   storing the ball center coordinate and the diameter in a device independent packet format (DIPF) based on the extensible markup language (XML).

4. The method of claim 2, wherein building the first grid model further comprises building a second grid model that includes a horizontal ball distance and a vertical ball distance between two adjacent balls, a ball orientation, and a top-left corner ball coordinate.

5. The method of claim 4, wherein the step of building the second grid model further comprises:
   determining the horizontal ball distance dx from the maximum frequency of the minimum horizontal distance histogram as follows:

$$dx = \frac{\sum_{i=1}^{M} dmx_i}{M}$$

where $dmx_i$ is the minimum horizontal distance of the ith ball located inside the maximum bin of the histogram, and M is the total number of balls located in the maximum frequency bin of the histogram; and
   storing the horizontal ball distance in the DIPF format in the internal memory.

6. The method of claim 4, wherein the step of building the second grid model further comprises:
   determining the vertical ball distance dy from the maximum frequency of the minimum vertical distance histogram as follows:

$$dy = \frac{\sum_{i=1}^{M} dmy_i}{M}$$

where $dmy_i$ is the minimum vertical distance of the ith ball located inside the maximum bin of the histogram, and M is the total number of balls located in the maximum frequency bin of the histogram; and
   storing the vertical ball distance in the DIPF format in the internal memory.

7. The method of claim 6, wherein the step of building the second grid model further comprises the step of obtaining the BGA ball orientation θ as follows:

$$\theta = \frac{\theta_h + 90° - \theta_v}{2}$$

where $\theta_h$ is a ball horizontal angle, and $\theta_v$ is a ball vertical angle; and storing the vertical ball distance in the DIPF format in the internal memory.

8. The method of claim 7, wherein the step of building the second grid model further comprises the step of determining the BGA top-left corner coordinator that is defined as an intersection of a first row gird line and a first column grid line, wherein the first row grid line is generated by connecting centers of the first ball and the last ball in the first row, the first column grid line being generated by connecting centers of the first ball and the last ball in the first column.

9. The method of claim 4, further including the step of building a third grid model, comprising:
fine-tuning a horizontal and vertical inter-ball distance by averaging inter-ball distances of all rows/columns to further tune BGA model parameters;
fine-tuning a BGA ball orientation by averaging each horizontal angle and each vertical angle, wherein the angles are determined between two adjacent balls;
fine-tuning a BGA top-left corner coordinate by using local and global BGA ball contrast calculation; and
storing a fine-tuned horizontal and vertical inter-ball distance, a fine-tuned BGA ball orientation, and a fine-tuned BGA top-left corner coordinate in the DIPF format in the internal memory.

10. The method of claim 9, the step of fine-tuning the BGA ball orientation further comprising applying $$\theta = \frac{\theta_h + 90° - \theta_v}{2}$$

again, wherein the first and last balls in each row/column are used to have the longest distance, and wherein $\theta_h$, or $\theta_v$ is an averaged horizontal angle and vertical angle, respectively.

11. The method of claim 1, wherein generating the second geometric model further comprises:
setting a plurality of regions of interest (ROIs) containing the body of the BGA to be modeled;
detecting four body boundaries of the body to localize four corner coordinates; and
determining the body orientation from orientations of four boundaries.

12. The method of claim 11, wherein determining the body orientation further comprises:
projecting an image having an edge along a radial line oriented at an angle of ($\phi+90°$), wherein $\phi$ is an orientation of a body boundary edge line and maximum value of the projection equals to the integral value of the body boundary edge line.

13. The method of claim 12, wherein the maximum value of the projection is decreased when the body boundary edge line is projected at ($\phi+90°\pm\Delta\phi$), where $\Delta\phi\neq0$.

14. The method of claim 12, further comprising the step of:
projecting the body boundary edge line in the range of ($\phi_1+90°$) to ($\phi_2+90°$) to obtain a profile of the maximum projection value at each angle, wherein the orientation of the body boundary edge line is in the range of ($\phi_1,\phi_2$).

15. The method of claim 11, further comprising the step of:
identifying four edges of the BGA body by edge detection operation.

16. The method of claim 15, further comprising the step of:
performing orientation determination for the left, top, right and bottom edges to obtain corresponding edge orientation.

17. The method of claim 11, the body orientation is determined by the step of:
calculating the body orientation $\phi$ as follows:

$$\phi = \frac{(90-\phi_l)+\phi_t+(90-\phi_r)+\phi_b}{4},$$

where $\phi_l$, $\phi_t$, $\phi_r$, or $\phi_b$ is an orientation for the left, the top, the right, or the bottom orientation, respectively.

18. The method of claim 11, further comprising the step of:
calculating intersection positions of two adjacent boundary lines to obtain four corner coordinates to localize of four boundaries.

19. A computer-implemented method for modeling a ball grid array (BGA) body in semiconductor surface mounted devices, the method comprising the steps of:
setting a plurality of regions of interest (ROIs) containing the BGA body;
performing orientation determination for left, top, right and bottom edges of the BGA body to obtain corresponding edge orientation;
determining an orientation of the BGA body by calculating the body orientation $\phi$ as:

$$\phi = \frac{(90-\phi_l)+\phi_t+(90-\phi_r)+\phi_b}{4},$$

where $\phi_l$, $\phi_t$, $\phi_r$, and $\phi_b$ are the edge orientations for the left, the top, the right, or the bottom orientation, respectively; and
localizing four corner coordinates to detect four body boundaries by calculating intersection positions of two adjacent boundary lines.

20. A program storage device readable by machine, tangibly embodying a program of instructions executable by the machine to perform method steps for inspecting ball grid array (BGA) components using a model thereof in semiconductor surface mounted devices, the method steps comprising:
setting a plurality of regions of interest (ROIs) for all BGA balls to be modeled;
building a first grid model that includes coordinates and a diameter of the BGA balls in the plurality of ROIs;
setting a plurality of regions of interest (ROIs) containing a BGA body to be modeled;
detecting four body boundaries to localize four corner coordinates;
determining a body orientation from orientations of four boundaries;
calculating an orientation of each boundary by the projection of the edge of boundary; and
comparing the BGA components with an obtained BGA model to inspect the BGA components based on ball positions, diameter, inter-ball distance, a total number of the BGA balls, body size, or body orientation.

21. The program storage device of claim 20, wherein the step of building the first grid model further comprises:
detecting whether a ball exists in the inside of each ROI to extract ball information using dominant circle detection process;
calculating a ball center coordinate and a diameter of each detected ball if a ball is detected; and
storing the ball center coordinate and the diameter in a device independent packet format (DIPF) based on the extensible markup language (XML).

22. The program storage device of claim 21, wherein the step of modeling ball grid array balls further comprises building a second grid model that includes a horizontal ball distance and a vertical ball distance between two adjacent balls, a ball orientation, and a top-left corner ball coordinate.

23. The program storage device of claim 22, further including the step of building a third grid model, comprising:
fine-tuning a horizontal and vertical inter-ball distance by averaging inter-ball distances of all rows/columns to further tune BGA model parameters;
fine-tuning a BGA ball orientation by averaging each horizontal angle and each vertical angle, wherein the angles are determined between two adjacent balls;
fine-tuning a BGA top-left corner coordinate by using local and global BGA ball contrast calculation; and
storing a fine-tuned horizontal and vertical inter-ball distance, a fine-tuned BGA ball orientation, and a fine-tuned BGA top-left corner coordinate in the DIPF format in the internal memory.

24. The program storage device of claim 23, further comprising the step of:
identifying four edges of the BGA body by edge detection operation.

25. The program storage device of claim 24, further comprising the step of:
performing orientation determination for the left, top, right and bottom edges of the BGA body to obtain corresponding edge orientation.

26. The program storage device of claim 25, further comprising the step of:
calculating intersection positions of two adjacent boundary lines of the BGA body to obtain four corner coordinates to localize of four boundaries.

* * * * *